(12) United States Patent
Hopmann et al.

(10) Patent No.: US 6,596,518 B2
(45) Date of Patent: Jul. 22, 2003

(54) PERCYQUINNIN, A PROCESS FOR ITS PRODUCTION AND ITS USE AS A PHARMACEUTICAL

(75) Inventors: Cordula Hopmann, Frankfurt am Main (DE); Michael Kurz, Hofheim (DE); Guenter Mueller, Sulzbach (DE); Luigi Toti, Hochheim am Main (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/826,866

(22) Filed: Apr. 6, 2001

(65) Prior Publication Data

US 2002/0039768 A1 Apr. 4, 2002

(30) Foreign Application Priority Data

Apr. 7, 2000 (EP) .............................................. 00107536

(51) Int. Cl.$^7$ ........................... C12P 17/02; A61K 35/84
(52) U.S. Cl. .................................. 435/123; 424/195.15
(58) Field of Search ..................... 424/195.15; 435/123

(56) References Cited

FOREIGN PATENT DOCUMENTS

| GB | 1 538 717 | 1/1979 |
|----|-----------|--------|
| WO | WO 93/21338 | 10/1993 |

OTHER PUBLICATIONS

House, H.O., "Alkyl Halides from Olefins or Alcohols," *Modern Synthetic Reactions*, 2$^{nd}$ edition, 446–452, (1972).
March, J., et al., Advances Organic Synthesis, 4$^{th}$ Edition "Hydrogenation of Double and Triple Bonds," 771–775 (1992).
Smith, M., et al., "Carbodiimides. VII. Observations of the Reactions of Carbodiimides with Acids and Some New Applications in the Synthesis of Phosphoric Acid Esters," *J. Am. Chem. Soc.*, 80: 6204–6212, (1958).
Arrieta, A., et al., "Reagents and Synthetic Methods 28. Modified Procedures for Anhydrization, Esterification and Thiolesterification of Carboxylic Acids by Means of Available Phosphorus Reagents," *Synth. Commun.*, 13: 471–487, (1983).
Benjymin, W.A., et al., "Alkyl Halides from Olefins or Alcohols," *Modern Synthetic Reactions*, 446–452, (1972).
Schroder, M., "Osmium Tetraoxide Cis Hydroxylation of Unsaturated Substrates," *Chem. Rev.*, 80: 187–213, (1980).
Brimble, M.A., et al., "Synthesis of a New Spiroacetal Based Herbicide," *Tetrahedron Letters*, 38: 3591–3594, (1997).
Bestmann, H.J. and Vostrowsky, O., "Selected Topics of the Wittig Reaction in the Synthesis of Natural Products," *Topics in Current Chem.*, 109: 85–163, (1983).
Bloch, R., et al., "Synthesis of Both Enantiomers of gamma–Substituted α, β–Unsaturated gamma–Lactones," *J. Org. Chem.*, 52: 4603–4605, (1987).
Pearson, A.J. and Hsu S–Y., "Ester–Directed Alkene Functionalization. A Potential Approach to Trichothecene Sythensis," *J. Org. Chem.*, 51: 2505–1511, (1986).

*Primary Examiner*—Christopher R. Tate
*Assistant Examiner*—Kailash C. Srivastava
(74) *Attorney, Agent, or Firm*—Finnegan, Henderson, Farabow, Garrett & Dunner, LLP

(57) ABSTRACT

The present invention relates to a compound named Percyquinnin that is obtainable by cultivating a basidiomycetes *Stereum complicatum* (DSM 13303), and to its pharmaceutically acceptable salts. The present invention further relates to a process for the production of Percyquinnin and to the use of Percyquinnin and its pharmaceutically acceptable salts as pharmaceuticals, in particular to their use as inhibitors of lipase.

17 Claims, No Drawings

PERCYQUINNIN, A PROCESS FOR ITS PRODUCTION AND ITS USE AS A PHARMACEUTICAL

This invention relates to a compound named Percyquinnin, its pharmaceutically acceptable salts and derivatives, and to methods for obtaining the compound. One method of obtaining the compound is by cultivation of the Basidiomycete *Stereum complicatum*, ST 001837 (DSM 13303). The present invention further relates to a process for the production of Percyquinnin, to the fungus ST 001837 (DSM 13303), to the use of Percyquinnin and its pharmaceutically acceptable salts and derivatives as pharmaceuticals, in particular to their use as lipase inhibitors, and to pharmaceutical compositions comprising Percyquinnin or a pharmaceutically acceptable salt or derivative thereof.

Lipid metabolism normally keeps a delicate balance between synthesis and degradation. When the balance is upset, hyperlipidemia may occur, which in turn can cause atherosclerosis, hypertension, diabetes etc. Modulators of lipid metabolism may be expected to be useful in controlling these and other disorders.

Inhibition of lipolysis in non-insulin-dependent diabetes mellitus (NIDDM) is supposed to reduce hyperglycemia. The initial event in the utilization of fat as an energy source is the hydrolysis of triacylglycerol by lipases, e.g., hormone sensitive lipase, and monoacylglycerol lipase. Hydrolyses of triacylglycerols may lead to increased levels of glycerol and fatty acids in the blood. Lipase inhibitors may be expected to reduce both plasma fatty acid levels and hyperglycemia with reduced side effects.

Obesity and hypercholesterolemia may be to a relevant degree related to high nutritional fat intake. An enzyme involved in dietary triglyceride absorption is pancreatic lipase. Inhibition of pancreatic lipase may therefore result in inhibition of fat absorption.

It has now been found that a novel compound named Percyquinnin inhibits lipase. The present invention thus relates to Percyquinnin, a compound of the formula:

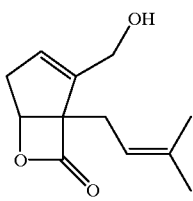

and to its pharmaceutically acceptable salts and derivatives, such as esters, ethers and obvious chemical equivalents, including all stereoisomeric forms and all tautomeric forms.

Percyquinnin has the molecular formula $C_{12}H_{16}O_3$ (208 Da) and may be characterized by any one or more of its physico-chemical and spectral properties given below, such as its $^1H$ NMR spectroscopic data and its $^{13}C$ NMR spectroscopic data, provided in Tables 1 and 2.

Percyquinnin may be described as a new β-lactone with an annelated five membered ring carrying a hydroxymethyl moiety and a 2,3-isopentenyl sidechain at the α-position of the lactone. Percyquinnin has a hitherto unreported new structure. A chemical abstract literature search established Percyquinnin to be a new compound.

A method for obtaining Percyquinnin is by cultivation of a microorganism referred to as Culture No. ST 001837 (henceforth referred to as ST 001837). This fungus, used for the production of Percyquinnin, was collected at Percy Quinn, Mississippi State Park in Pike County, USA. The fungus ST 001837 belongs to the order of Basidiomycetes species *Stereum complicatum* and was deposited according to the rules of the Budapest Convention on Feb. 4, 2000 with the German Collection of Microorganisms and Cell Cultures (DSMZ—Deutsche Sammlung von Mikroorganismen und Zelikulturen GmbH), Mascheroder Weg 1B, D-38124 Braunschweig, Germany and has been given the accession number DSM No. 13303.

Thus, the present invention further provides a process for the production of the novel compound named Percyquinnin from Basidiomycetes species ST 001837, and from its Basidiomycete mutants and variants, under aerobic conditions in a nutrient medium comprising at least one source of carbon atoms and at least one source of nitrogen atoms and optionally further comprising at least one component chosen from nutrient inorganic salts and trace elements, followed by isolation of said compound and purification in a customary manner.

The nutrient medium comprises at least one source of carbon atoms, at least one source of nitrogen atoms and optionally comprises at least one nutrient inorganic salt. The carbon atom sources may be chosen from a variety of sources, examples include starches, glucose, sucrose, dextrins, fructose, molasses, glycerol, lactose and galactose. In one embodiment, the carbon atom source is glucose. The nitrogen atom sources may be chosen from a variety of sources; examples include soyabean meals, peanut meals, yeast extracts, beef extracts, peptones, malt extracts, corn steep liquors, gelatins and casamion acids. In one embodiment, the nitrogen atom source is chosen from malt extracts and yeast extracts. The nutrient inorganic salts may be chosen from a variety of salts; examples include sodium hydrogen phosphate, potassium hydrogen phosphate, ammonium hydrogen phosphate, sodium chloride, calcium chloride, calcium carbonate, potassium nitrate, ammonium sulphate and magnesium sulphate. In one embodiment, the nutrient inorganic salt is ammonium hydrogen phosphate.

The cultivation of ST 001837 may be carried out at temperatures ranging from 20 to 35° C. and at a pH ranging from 3.0 to 8.0. In one embodiment, ST 001837 is cultivated at 25° C. (±1° C.) and at a pH ranging from 3 to 5.

In one embodiment, the cultivation of ST 001837 is carried out for a time period ranging from 96 to 300 hours. During this time period, a yield of the lipase inhibitor Percyquinnin of the invention may be obtained. In a further embodiment, the cultivation by fermentation is carried out for a time period ranging from 216 to 264 hours under submerged conditions. Examples of submerged conditions include being in containers chosen from shake flasks and laboratory fermenters. The progress of fermentation and formation of the Percyquinnin can be detected by High Pressure Liquid Chromatography (HPLC) and by measuring the bioactivity of the culture broth. In the resulting culture broth, Percyquinnin is present in the culture filtrate and in mycelium. In one embodiment, the Percyquinnin is isolated from the mycelium. Percyquinnin can be isolated using known separation techniques. For example, one method for recovering Percyquinnin from the culture filtrate is by extraction with a water immiscible solvent, examples include ethyl acetate, dichloromethane, chloroform and butanol, at a pH ranging from 5 to 8.

Another method for recovering Percyquinnin, for example, is by hydrophobic interaction chromatography using polymeric resins; examples include "Diaion HP-20®", "MCl® Gel CHP-20P" (Mitsubishi Chemical Industries Limited, Japan), and "Amberlite XAD®" (Rohm and Hass Industries U.S.A.), and activated charcoal. Another separation method may be ion exchange chromatography at a pH ranging from 5 to 8. In one embodiment, the Percyquinnin is recovered using chromatography on MCI® Gel CHP-20P. The active material can also be recovered from mycelium by extraction with a water miscible solvent, examples include methanol, acetone, acetonitrile, n-propanol and iso-propanol, or a water immiscible solvent, examples include ethyl acetate, dichloromethane, chloroform and butanol, at a pH ranging from 5 to 8. In one embodiment, the Percyquinnin is extracted from mycelium using methanol as a solvent. Extracts may be further concentrated and lyophilized to give the active crude material.

The inhibitor Percyquinnin of the present invention may, for example, be recovered from the crude material by fractionation using any of the following techniques:

normal phase chromatography (using alumina or silica gel as stationary phase and eluents such as petroleum ether, ethyl acetate, methylene chloride, acetone, chloroform, methanol or combinations thereof and additions of amines such as $NEt_3$), reverse phase chromatography (using reverse phase silica gel such as dimethyloctadecylsilyl-silica gel, also called RP-18 or dimethyloctylsilyl silica gel also called RP-8 as stationary phase and eluents such as water, buffers viz. phosphate, acetate, citrate (pH 2–8) and organic solvents such as methanol, acetonitrile, acetone, tetrahydrofuran or combinations of these solvents), gel permeation chromatography using resins such as ®Sephadex LH-20 (Pharmacia Chemical Industries, Sweden), TSKgel ®Toyopearl HW (TosoHaas, Tosoh Corporation, Japan) in solvents such as methanol, chloroform, acetone, ethyl acetate or their combinations or ®Sephadex G-10 and G-25 in water;

or by counter-current chromatography using a biphasic eluent system made up of at least two solvents such as water, methanol, ethanol, iso-propanol, n-propanol, tetrahydrofuran, acetone, acetonitrile, methylene chloride, chloroform, ethyl acetate, petroleum ether, benzene and toluene.

These techniques may be used repeatedly. A combination of the different techniques may also be used. In one embodiment, the Percyquinnin is recovered from the crude material by chromatography over reverse phase silica gel (RP-18).

Percyquinnin may be converted into pharmaceutically acceptable salts and derivatives, such as esters, ethers and other obvious chemical equivalents, which are all covered by the present invention. The salts and derivatives can be prepared by standard procedures known to one skilled in the art. Salts such as sodium and potassium salts, for example, may be prepared by treating Percyquinnin with suitable sodium or potassium bases. Other salts may be prepared in a similar manner.

Esters and ethers may be prepared by methods known in the literature, for example, in Advanced Organic Synthesis, $4^{th}$ Edition, J. March, John Wiley & Sons., (1992). Esters may be formed by reaction with carboxylic acids, including amino acids, such as leucine, glycine or alanine. The amino group of the amino acid may be deprotected after esterification or protected, for example with a formyl group. Esterification may be done in the presence of a dehydrating agent, for example dicyclohexylcarbodiimid (DCC) as described in the literature (Smith et al., *J. Am. Chem. Soc.* (1958) 80, 6204; Arrieta et al. *Synth. Commun* (1983), 13,471).

The double bonds may be reduced by the methods given in the literature, for example, in P. N. Rylander, "Hydrogenation Methods", Academic Press, New York (1985), Chapter 2. Double bonds may be hydrohalogenated by methods described by H. O. House in "Modern Synthetic Reactions", W. A. Benjymin, Inc., New York (1972), pp 446–452. Hydroxylated derivatives may be produced by reaction of the double bonds with reagents like $OsO_4$ as described in the literature, for example in *Chem. Rev.* (1980), 80, 187.

Derivatives may also be formed by conversion of the double bonds into epoxides by oxidation, for example with MCPBA as described in Advanced Organic Synthesis, $4^{th}$ Edition, J. March, John Wiley & Sons., (1992).

Derivatives may also be formed by ozonolysis of the double bond of the isopentenyl side chain. Depending on the work-up procedure, this may result in an aldehyde (for example with Zn/HOAc or dimethylsulfid/methanol), or may result in carboxylic acid (for example with $H_2O_2$) or may result in an alcohol (for example with $LiAlH_4$ or $NaBH_4$) as a functional group [W. Curruthers, "Some Modern Methods of Organic Synthesis", Cambridge University Press (1971), Chapter 6; White, King and O'Brien, *Tetrahedron Lett.* 3591 (1971); Bailey, P. S., "Ozonisation in Organic Chemistry", Vol. 1 and Vol. 2, New York, Academic Press (1978, 1982)].

Reaction of the so formed aldehydes with phosphoranes, known in the literature as the Wittig reaction, results in the introduction of side chains with 4 to 10 carbon atoms. The newly introduced side chains may be optionally substituted with additional groups. For example, $OR^1$ ($R^1$=H or alkyl with 1 to 4 carbon atoms), $NR^2R^3$ ($R^2R^3$=H or alkyl with 1 to 4 carbon atoms), F, Cl, Br or I as functional groups was described in: H. J. Bestmann et al., "Selected Topics of the Wittig Reaction in the Synthesis of Natural Products", Topics in Current Chemistry (1983) 109, 85.

Percyquinnin shows inhibition of lipase with an $IC_{50}$ of 2 $\mu M$ (NBD-assay, see Example 6).

The invention also relates to the use of Percyquinnin in the form of its racemates, racemic mixtures and pure enantiomers, and to its diastereomers and mixtures thereof.

Pharmaceutically acceptable salts may be particularly suitable for medical applications because of their greater solubility in water compared with the initial compounds on which they are based. These salts must have a pharmaceutically acceptable anion or cation. Suitable pharmaceutically acceptable acid addition salts of Percyquinnin may be salts of inorganic acids such as hydrochloric acid, hydrobromic acid, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. In one embodiment, the chloride is used for medical purposes. Suitable pharmaceutically acceptable basic salts may be ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in non-therapeutic, for example in vitro, applications.

The term "physiologically functional derivative" used herein refers to any physiologically tolerated derivative of a compound according to the invention, for example an ester, which may be administered to a mammal, such as, for example, to humans, to form (directly or indirectly) such a compound or an active metabolite thereof.

A further aspect of this invention is the use of prodrugs of Percyquinnin. The term "prodrug" used herein refers to a compound which can be metabolized to form a second compound of interest. For example, prodrugs of Percyquinin can be metabolized in vivo to form a compound chosen from Percyquinnin, a Percyquinnin salt, a Percyquinnin solvate and a physiologically functional derivative thereof as described herein. These prodrugs may themselves be active or not.

Percyquinnin may also exist in various polymorphous forms, for example as amorphous and crystalline polymorphous forms. All polymorphous forms of Percyquinnin fall within the scope of the invention and are a further aspect of the invention.

All references hereinafter to Percyquinnin refer to Percyquinnin as described above and to the salts, solvates and physiologically functional derivatives thereof as described herein.

The amount of Percyquinnin necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram body weight, for example 3–10 mg/kg/day. An intravenous dose may be, for example, in the range from 0.3 mg to 1.0 mg/kg, which can suitably be administered as an infusion of 10 ng to 100 ng per kilogram and per minute. Infusion solutions suitable for these purposes may have a concentration, for example, ranging from 0.1 ng to 10 mg, typically from 1 ng to 10 mg, per milliliter. Single doses may have a concentration, for example, ranging from 1 mg to 10 g of the active ingredient. Thus, ampoules for injections may have a concentration, for example, ranging from 1 mg to 100 mg, and single dose formulations which can be administered orally, such as, for example, tablets or capsules, may have a concentration, for example, ranging from 1.0 to 1000 mg, typically from 10 to 600 mg. In the case of pharmaceutically acceptable salts, the above weight data are based on the weight of the aminothiazole ion derived from the salt. Percyquinnin as a compound can be used for prophylaxis or therapy of the above mentioned states (such as disorders of lipid metabolism), but they may also be treated or prevented using Percyquinnin in the form of a pharmaceutical composition with a compatible carrier.

The carrier must, of course, be compatible in the sense of compatibility with other ingredients of the composition and not be harmful to the patient's health. The carrier may be a solid or a liquid or both and may be formulated with the compound as single dose, for example as tablet, which may have a concentration, for example, ranging from 0.05% to 95% by weight of the active ingredient. The pharmaceutical compositions according to the invention may be produced by one of the known pharmaceutical methods which comprises mixing the ingredients with pharmacologically acceptable carriers and/or excipients.

Pharmaceutical compositions according to the invention may be those suitable for oral, rectal, topical, peroral (for example sublingual) and parenteral (for example, subcutaneous, intramuscular, intradermal or intravenous) administration, although the mode of administration depends in each individual case on the nature and severity of the condition to be treated and on the nature of Percyquinnin used in each case. Coated formulations and coated slow-release formulations also fall within the scope of the invention. Acid- and gastric fluid-resistant formulations are possible embodiments. Suitable gastric fluid-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, pastilles and tablets, each of which may comprise a defined amount of Percyquinnin; as powder; as granules; as solution; as suspension in an aqueous or nonaqueous liquid; as an oil-in-water; and as a water-in-oil emulsion. These compositions may, as already mentioned, be prepared by any suitable pharmaceutical method which includes a step in which the active ingredient and the carrier (which may optionally further comprise at least one additional ingredient) are brought into contact. In general, the compositions may be produced by uniform and homogeneous mixing of the active ingredient with a carrier chosen from a liquid carrier and a finely dispersed solid carrier, after which the product may be optionally shaped. Thus, for example, a tablet can be produced by compressing or shaping the powder or granules of the compound, where appropriate with at least one additional ingredient. Compressed tablets may be produced by tabletting the compound in free-flowing form, such as, for example, a powder or granules, optionally further comprising at least one component chosen from binders, lubricants, inert diluents, surface-active agents and dispersing agents in a suitable machine. Shaped tablets can be produced by shaping, in a suitable machine, the compound which is in powder form and has been optionally moistened with at least one inert liquid diluent.

Pharmaceutical compositions suitable for peroral (sublingual) administration comprise Percyquinnin and optionally further comprise at least one flavoring. Flavorings include, for example, sucrose, gum arabic, and tragacanth. Pharmaceutical compositions suitable for peroral (sublingual) administration may be in any suitable form. Suitable forms include, for example, suckable tablets and pastilles. Pastilles may comprise Percyquinnin and at least one inert base. The inert base may be chosen from gelatin, glycerol, sucrose and gum arabic, for example.

Suitable pharmaceutical compositions for parenteral administration may comprise sterile aqueous preparations of Percyquinnin, which may be isotonic with the blood of the intended recipient. These preparations may be administered intravenously, although administration can also take place by subcutaneous, intramuscular or intradermal injection. These preparations can be produced by mixing the compound with water and making the resulting solution sterile and isotonic with blood. Injectable compositions according to the invention generally present in a concentration ranging from 0.1 to 5% by weight of the active compound.

Suitable pharmaceutical compositions for rectal administration may be in the form of single-dose suppositories. These can be produced by mixing Percyquinnin with at least one conventional solid carrier, for example, cocoa butter, and shaping the resulting mixture.

Suitable pharmaceutical compositions for topical use on the skin may be in any suitable form. Suitable forms include, for example, ointments, creams, lotions, pastes, sprays, aerosols and oils. Carriers which can be used may be, for example, petrolatum, lanolin, polyethylene glycols, alcohols and combinations of at least two of these substances. The active ingredient is generally present in a concentration ranging from 0.1 to 15% by weight of the composition, for example from 0.5 to 2%.

Transdermal administration is also possible. Suitable pharmaceutical compositions for transdermal applications may be in the form of single plasters which may be suitable for long-term close contact with the patient's epidermis. Plasters of this type suitably comprise the active ingredient in an aqueous solution which is optionally buffered where appropriate, dissolved and/or dispersed in an adhesive or dispersed in a polymer. A suitable active is ingredient concentration ranges from about 1% to 35%, for example from about 3% to 15%. As a particular option, the active ingredient can be released by electrotransport or iontophoresis as described, for example, in Pharmaceutical Research, 2 (6): 318 (1986).

The following examples are intended to illustrate the invention without limiting the scope thereof.

EXAMPLE 1

Maintenance of the Culture ST 001837
a) Composition of Maintenance Medium

After dissolving the ingredients thoroughly by heating, the resultant solution was sterilized at 121° C. for 20 min and distributed in Petri dishes (15 ml/dish). After solidification the plates were inoculated with the start culture and incubated at 25° C. until good growth was observed. The well-grown cultures were used for the following conservation steps.

Maintenance Medium

|  | % |
| --- | --- |
| Malt extract | 2.00 |
| Yeast extract | 1.00 |
| Glucose | 1.00 |
| $(NH_4)_2HPO_4$ | 0.05 |
| Agar—Agar | 2.00 | b) Conservation at −135° C.:

1.5 ml of a sterile 10% DMSO solution was poured into 2 ml cryo vials. From the maintenance agar plate, a 2 cm² agar piece is added to the DMSO solution, step freezed (1° C. per min) and stored at −135° C.

c) Conservation in Liquid Nitrogen:

1.5 ml of a sterile 50% glycerol solution were poured into 2 ml cryo vials. From the maintenance agar plate, a 2 cm² agar piece was taken and added to the glycerol solution, step freezed (1° C. per min) until −80° C. and then stored in liquid nitrogen.

EXAMPLE 2

Fermentation of the Culture No. ST 001837 in Shake Flasks
Preparation of Seed Culture in Shake Flasks The seed medium (see below) was distributed in 100 ml amounts in 300 ml shake flasks and autoclaved at 121° C. for 20 minutes. The flasks were cooled to room temperature and inoculated with 2 cm² agar pieces taken from a 6 day old agar plate culture or with the content of one conservation vial (−135° C. or liquid nitrogen). The incubation was carried out for 96 hours on a rotary shaker at 140 rpm and 25° C.

Seed Medium

|  | % |
| --- | --- |
| Corn steep liquid | 0.50 |
| Tomato paste | 4.00 |
| Oatmeal | 1.00 |
| Glucose | 1.00 |
| Trace elements | 1.00 ml |
| pH 6.8 | |

Trace Element Solution

|  | % |
| --- | --- |
| $FeSO_4 \times 7H_2O$ | 0.1000 |
| $MnSO_4 \times 1H_2O$ | 0.1000 |
| $CuCl_2 \times 2H_2O$ | 0.0025 |
| $CaCl_2 \times 2H_2O$ | 0.0100 |
| $H_3BO_3$ | 0.0056 |
| $(NH_4)_6Mo_7O_{24} \times 4H_2O$ | 0.0019 |
| $ZnSO_4 \times 7H_2O$ | 0.0200 |

Production Conditions

The production medium (see below) was distributed in 100 ml amounts in 300 ml shake flasks and autoclaved at 121° C. for 20 minutes. The flasks were cooled to room temperature and inoculated with 2 ml of 4 days old seed culture. The incubation was carried out for 240 hours on a rotary shaker at 140 rpm and 25° C. The production of the inhibitor Percyquinnin was determined by testing the bioactivity against the inhibition of lipase as described (Example 6) and by HPLC analysis.

Production Medium

|  | % |
| --- | --- |
| Malt extract | 2.00 |
| Yeast extract | 0.20 |
| Glucose | 1.00 |
| $(NH_4)_2HPO_4$ | 0.05 |

EXAMPLE 3

Cultivation of the Culture No. ST 001837 in Fermenters (12 L)
Preparation of Seed Culture in Shake Flasks The seed medium was distributed in 500 ml amounts in 2 L Erlenmeyer flasks and autoclaved at 121° C. for 30 min The seed culture was grown in these flasks as described in Example 2.

Large Scale Fermentation
Composition of Production Medium:

8 L of the production medium in 12 L fermenter (in two fermenters) along with 1 ml (/10 L fermenter) of ®Desmophen as an antifoaming agent were sterilized in situ for 45 min at 121° C., cooled to 25° C. (±1° C.) and seeded with 0.5 L (6.25% of 12 L. fermenter) of the seed culture mentioned above.

The fermentation was run with the following parameters:

| Temperature | 25° C. |
| --- | --- |
| Agitation | 300 rpm ($v_{tip}$ = 1.57 m/s) |
| Aeration | 0.5 vvm |
| Harvest time | 237 h |

The production of the lipase inhibitor Percyquinnin was determined by testing the inhibition of lipase as described in Example 6. The final pH of the culture broth was 3 to 4. The culture broth was harvested and centrifuged and the compound Percyquinnin was isolated and purified from the culture filtrate and the mycelium by the method described in Example 4.

EXAMPLE 4
Isolation and Purification of Percyquinnin

The culture broth (3 liters) was harvested and centrifuged to separate the mycelium (20 g) and culture filtrate. The mycelium was extracted with methanol (3 liters) and the active extracts were pooled and concentrated under reduced pressure to a volume of 50 ml. This crude material was purified by preparative HPLC using the following conditions:

% 1.) Column: MCI® Gel CHP-20P (BioCart, 50×100 mm; Kronlab)

| Eluent: | A) $H_2O$ | | B) MeOH |
|---|---|---|---|
| Gradient: | min | % A | % B |
| | 0 | 95 | 5 |
| | 5 | 95 | 5 |
| | 45 | 0 | 100 |
| Flow: | 45 ml/min | | |
| Detection: | 220 und 254 nm | | |

The active fractions eluted after 17 min. The pooled fractions were concentrated under reduced pressure and freeze dried.

The final purification was done by preparative HPLC using the following conditions:

1.) Column: Purospher Star RP-18e (5μ, 125×25 mm, Merck)

| Eluent: | A) 0.1% TFA | | B) $CH_3CN$ |
|---|---|---|---|
| Gradient: | min | % A | % B |
| | 0 | 95 | 5 |
| | 5 | 95 | 5 |
| | 45 | 0 | 100 |
| Flow Rate: | 38 ml/min | | |
| Detection: | 210 und 300 nm | | |

The Percyquinnin containing fractions eluted after 21 min. The pooled fractions were concentrated under reduced pressure and freeze dried.

2.) Column: Purospher RP-18e (5μ, 125×25 mm, Merck)

| Eluent: | A) 0.1% TFA | | B) $CH_3CN$ |
|---|---|---|---|
| Gradient: | min | % A | % B |
| | 0 | 80 | 20 |
| | 10 | 80 | 20 |
| | 10.1 | 75 | 25 |
| | 17 | 75 | 25 |
| | 17.1 | 70 | 30 |
| | 50 | 70 | 30 |
| | 55 | 0 | 100 |
| | 100 | 0 | 100 |
| Flow Rate: | 5 ml/min | | |
| Detection: | 210 nm | | |

The Percyquinnin containing fractions eluted after 37 min. The pooled fractions were concentrated under reduced pressure and freeze dried. The overall yield from 20 g to mycelium was 2 mg of the compound Percyquinnin.

The physico-chemical and spectral properties of Percyquinnin are given in Tables 1 and 2.

TABLE 1

| Appearance | pale yellow oil | |
|---|---|---|
| Solubility | Methanol, DMSO | |
| HPLC (High Pressure Liquid Chromatography) | Column: | Purospher Star RP.18e (Merck), 55 × 4 mm, 3 pm |
| | Eluent: | $CH_3CN$/0.01% $H_3PO_4$ (85%) |
| | Gradient: | time / % $CH_3CN$ |
| | | 0.00 / 5.0 |
| | | 3.00 / 95.0 |
| | | 5.00 / 95.0 |
| | | 6.00 / 5.0 |
| | | 10.00 / 5.0 |
| | Flow: | 2 ml/min |
| | Temp.: | 40° C. |
| | Detection: | 210 nm, 254, 280, 320, 380 |
| | Retention time: | 2.1 min |
| EI-MS (56 eV) | m/z = 208 Da [M$^+$] | |
| GC-MS (in CH2Cl2 + MSTFA, 56 eV) | m/z = 280 Da [M$^+$ − H + TMS] | |
| Mol. formula: | $C_{12}H_{16}O_3$ | |
| $^1$H NMR: | see Table 2 | |
| $^{13}$C NMR: | see Table 2 | |

TABLE 2

$^1$H and $^{13}$C NMR Spectroscopic Data of Percyquinnin in DMSO at 300 K.

| | $^1$H | $^{13}$C |
|---|---|---|
| 1 | — | 172.97 |
| 2 | — | 74.24 |
| 3 | — | 148.37 |
| 4 | 5.51 | 120.45 |
| 5 | 2.73/2.57 | 36.99 |
| 6 | 4.93 | 78.41 |
| 7 | 2.54/2.37 | 27.05 |
| 8 | 5.11 | 117.92 |
| 9 | — | 134.66 |
| 10 | 1.60 | 17.77 |
| 11 | 1.68 | 25.57 |
| 12 | 4.01 | 59.39 |
| 12-OH | 4.97 | — |

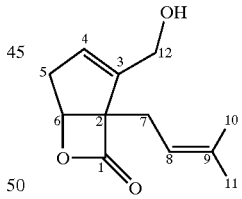

EXAMPLE 5
Preparation and Purification of Lipase

Adipocytes from male rats (Wistar 220–250 g) were isolated by collagenase treatment as described in the literature. The fat cells of 10 rats were washed three times each by flotation with 50 ml homogenization buffer (25 ml Tris/HCl, pH 7.4, 0.25 M sucrose, 1 mM EDTA, 1 mM DTT, 10 μg/ml Leupeptin, 10 μg/ml Antipain, 20 μg/ml Pepstatin). Afterwards 10 ml homogenization buffer was added. The fat cells were homogenized in a teflon-in-glass device (Braun-Melsungen) at 1500 rpm and 15° C. The homogeneous to product was centrifuged (Sorvall SM 24 tubes, 500 rpm, 10 min, 4° C.). The layer between the upper fat layer and the pellet was separated and centrifuged again. Separation of the under layer was repeated and centrifuged a third time at 2000 rpm for 45 min at 4° C. The resulting mother layer was added to 1 g Heparin Sepharose (Pharmacia-Biotech, CL-6B, washed five times with 25 mM Tris/HCl, pH 7.4, 150 mM NaCl). After incubation for 60 min at 4° C. (shaken in intervals of 15 min), the solution was centrifuged (Sorvall SM24 tubes, 3000 rpm, 10 min, 4° C.). The upper layer was adjusted to pH 5.2 with acetic acid and incubated for 30 min at 4° C. The precipitates were isolated by centrifugation (Sorvall SS34 tubes, 12000 rpm, 10 min, 4° C.) and suspended in 2.5 ml 20 mM Tris/HCl, pH 7.0, 1 mM EDTA, 65 mM NaCl, 13% sucrose, 1 mM DTT, 10 μg/ml Leupeptin/PepstatinAntipain. The suspension was dialyzed overnight at 4° C. against 25 mM Tris/HCl, pH 7.4, 50% glycerols, 1 mM DTT, 10 μg/ml Leupeptin, Pepstatin, Antipain and afterwards absorbed on a hydroxyapatit column (0.1 g/l ml suspension equilibrated with 10 mM potassium phosphate, pH 7.0, 30% glycerol, 1 mM DTT). The column was washed with the equilibration buffer for four times (flow: 20–30 ml/h). The lipase was eluted with 0.5 M potassium phosphate buffer. The product was dialyzed and concentrated (5–10 times) by ultrafiltration (Amicon Diaflo PM 10) at 4° C. The partially purified lipase can be stored for 4–6 weeks at −70° C.

EXAMPLE 6

Bioactivity Assay

A fluorescent lipid analog, mono-NBD-acylglycerol (NAG) was used as substrate, which shifts its color upon integration into phospholipid vesicles from 481 nm to 550 nm. The test compound dissolved in DMSO was diluted with assay buffer (25 mM Tris/HCl, pH 7.4, 150 mM NaCl) 1:5. To 2.5 μl of this solution 180 μl of sonicated substrate solution were added (20 μg/ml phosphatidylcholine, 10 μg/ml phosphatidylinositol, 50 μg/ml NAG in assay buffer). After preincubation at 30° C. for 15 min., 20 μl of enzyme solution, prediluted 1:2 in assay buffer were added and absorption at 485 nm was immediately measured. After 60 min., incubation at 30° C. absorption was determined again. The increase in absorbance at 480 nm was a measurement of the enzyme activity. The determination of $IC_{50}$ values was carried out using 10 concentrations of the freshly dissolved test compound. For data analysis, the software packet GRAPHIT, Elsvier-Biosoft was used.

Percyquinnin shows inhibition of lipase with an $IC_{50}$ of 2 μm.

What is claimed is:

1. A compound of formula (I):

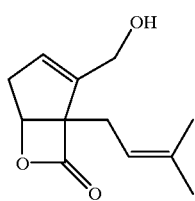

I or a pharmaceutically acceptable salt thereof.

2. Percyquinnin, a compound of the molecular formula $C_{12}H_{16}O_3$, obtained by cultivation of Basidiomycetes Stereum complicatum (DSM 13303), and mutants and variants thereof, wherein said compound has NMR data as shown in Table 2, and wherein said cultivation occurs under aerobic conditions in a nutrient medium comprising at least one source of carbon atoms and at least one source of nitrogen atoms, followed by isolation and purification of said compound in a customary manner, or a pharmaceutically acceptable salt thereof.

3. A composition comprising a compound chosen from a compound according to claim 1 or a compound according to claim 2, and an acceptable carrier.

4. A composition according to claim 3, wherein said composition is a pharmaceutical composition and said acceptable carrier is a pharmaceutically acceptable carrier.

5. A process for making a compound chosen from a compound according to claim 1 or a compound according to claim 2, comprising cultivation of Basidiomycetes Stereum complicatum (DSM 13303), and variants and mutants thereof, in a nutrient medium comprising at least one source of carbon atoms and at least one source of nitrogen atoms, and isolation and purification of said compound.

6. A process according to claim 5, wherein said cultivation occurs under aerobic conditions.

7. A process according to claim 5, wherein said carbon atom source is chosen from starches, glucose, sucrose, dextrins, fructose, molasses, glycerol, lactose and galactose.

8. A process according to claim 5, wherein said nitrogen atom source is chosen from soyabean meals, peanut meals, yeast extracts, beef extracts, peptones, malt extracts, corn steep liquors, gelatins and casamion acids.

9. A process according to claim 5, wherein said nutrient medium further comprises nutrient inorganic salts chosen from sodium hydrogen phosphate, potassium hydrogen phosphate, ammonium hydrogen phosphate, sodium chloride, calcium chloride, calcium carbonate, potassium nitrate, ammonium sulphate and magnesium sulphate.

10. A process according to claim 5, wherein said cultivation is carried out at a temperature ranging from 20 to 35° C. and at a pH ranging from 3.0 to 8.0.

11. A process according to claim 5, wherein said cultivation occurs during a time period ranging from 96 to 300 hours.

12. A process according to claim 5, wherein said cultivation occurs under submerged conditions.

13. A process according to claim 5, wherein said compound is isolated from at least one component chosen from culture filtrates and mycelia.

14. A process for inhibiting lipase, comprising contacting said lipase with an effective amount of a compound chosen from a compound according to claim 1 or a compound according to claim 2, sufficient to inhibit said lipase.

15. A process for inhibiting lipase according to claim 14, wherein said lipase is chosen from pancreatic lipase, hormone sensitive lipase, and monoacylglycerol lipase.

16. A process for inhibiting lipase in a mammal, comprising administering to said mammal an effective amount of a compound chosen from a compound according to claim 1 or a compound according to claim 2, sufficient to inhibit said lipase.

17. A process for inhibiting lipase according to claim 16, wherein said lipase is chosen from pancreatic lipase, hormone sensitive lipase, and monoacylglycerol lipase.

* * * * *